(12) United States Patent
Yoshida (10) Patent No.: US 7,932,501 B2
(45) Date of Patent: Apr. 26, 2011

(54) PARTICLE-BEAM EXPOSURE APPARATUS AND PARTICLE-BEAM THERAPEUTIC APPARATUS

(75) Inventor: Katsuhisa Yoshida, Tokyo (JP)

(73) Assignee: Mitsubishi Electric Corporation, Chiyoda-Ku, Tokyo (JP)

( * ) Notice: Subject to any disclaimer, the term of this patent is extended or adjusted under 35 U.S.C. 154(b) by 173 days.

(21) Appl. No.: 12/244,356

(22) Filed: Oct. 2, 2008

(65) Prior Publication Data

US 2009/0032721 A1 Feb. 5, 2009

Related U.S. Application Data

(62) Division of application No. 11/480,430, filed on Jul. 5, 2006, now Pat. No. 7,449,702.

(30) Foreign Application Priority Data

Jan. 16, 2006 (JP) ................................. 2006-007364

(51) Int. Cl.
*H01J 1/50* (2006.01)
(52) U.S. Cl. ............................ 250/396 ML; 250/396 R
(58) Field of Classification Search .................. None
See application file for complete search history.

(56) References Cited

U.S. PATENT DOCUMENTS

| 5,111,173 | A | * | 5/1992 | Matsuda et al. | 335/216 |
| 5,260,581 | A | * | 11/1993 | Lesyna et al. | 250/492.3 |
| 5,363,008 | A | * | 11/1994 | Hiramoto et al. | 313/62 |
| 5,789,875 | A | * | 8/1998 | Hiramoto et al. | 313/505 |
| 5,969,367 | A | * | 10/1999 | Hiramoto et al. | 250/492.3 |
| 6,218,675 | B1 | | 4/2001 | Akiyama et al. | |
| 6,316,776 | B1 | * | 11/2001 | Hiramoto et al. | 250/492.3 |
| 6,424,084 | B1 | * | 7/2002 | Kimiya et al. | 313/414 |
| 6,479,926 | B1 | * | 11/2002 | Awano et al. | 313/414 |
| 6,597,096 | B1 | * | 7/2003 | Amano et al. | 313/414 |
| 6,814,694 | B1 | * | 11/2004 | Pedroni | 600/1 |

(Continued)

FOREIGN PATENT DOCUMENTS

JP 11-197258 7/1999

(Continued)

*Primary Examiner* — Bernard E Souw
*Assistant Examiner* — Andrew Smyth
(74) *Attorney, Agent, or Firm* — Buchanan Ingersoll & Rooney PC (57) ABSTRACT

A particle-beam exposure apparatus and a particle-beam therapeutic apparatus are obtained, in which, by reducing diameter increase, due to scattering in a range shifter, of a charged particle beam, the charged particle beam whose diameter is so narrow that spatially accurate exposure into the target is possible can be supplied, as well as, by placing the range shifter at a position apart from a patient, intimidation caused by a movement noise, etc. can be prevented. A particle-beam exposure apparatus and a particle-beam therapeutic apparatus include a range shifter 4 for varying energy of a charged particle beam with a thickness of the range shifter 4 being changed during exposure of the charged particle beam, so that a range of the charged particle beam at a target 5 to be exposed is set to a desired value; and a set of quadrupole magnets 6, being placed between the range shifter 4 and the target 5, based on the magnetization amount of the set of quadrupole magnets 6 being controlled corresponding to the charged-particle-beam energy varied by the range shifter 4, for reducing diameter increase, due to scattering at the range shifter 4, of the charged particle beam at the target 5.

8 Claims, 5 Drawing Sheets

U.S. PATENT DOCUMENTS

| | | |
|---|---|---|
| 6,859,741 B2 | 2/2005 | Haberer et al. |
| 7,122,978 B2 * | 10/2006 | Nakanishi et al. ............. 315/500 |
| 7,154,107 B2 | 12/2006 | Yanagisawa et al. |
| 7,326,942 B2 * | 2/2008 | Shichi et al. ............. 250/492.21 |
| 7,449,701 B2 * | 11/2008 | Fujimaki et al. ........... 250/492.3 |
| 2004/0000650 A1 | 1/2004 | Yanagisawa et al. |
| 2004/0056212 A1 | 3/2004 | Yanagisawa et al. |
| 2004/0149934 A1 | 8/2004 | Yanagisawa et al. |
| 2004/0162457 A1 * | 8/2004 | Maggiore et al. .................. 600/1 |
| 2004/0200983 A1 * | 10/2004 | Fujimaki et al. ........... 250/492.3 |
| 2005/0231138 A1 * | 10/2005 | Nakanishi et al. ............. 315/500 |
| 2006/0065854 A1 * | 3/2006 | Shichi et al. ............. 250/492.21 |
| 2010/0213384 A1 * | 8/2010 | Furukawa et al. ..... 250/396 ML |

FOREIGN PATENT DOCUMENTS

| | | |
|---|---|---|
| JP | 2001-000562 | 1/2001 |
| JP | 2001-061978 | 3/2001 |
| JP | 2001-212253 | 8/2001 |
| JP | 2002-189004 | 7/2002 |
| JP | 2004-069683 | 3/2004 |
| JP | 2004-144538 | 5/2004 |
| JP | 2004-192931 | 7/2004 |
| JP | 2004-321830 | 11/2004 |

* cited by examiner

PARTICLE-BEAM EXPOSURE APPARATUS AND PARTICLE-BEAM THERAPEUTIC APPARATUS

BACKGROUND OF THE INVENTION

1. Field of the Invention

The present invention relates to particle-beam exposure apparatuses exposing, into targets to be exposed, charged particle beams supplied by particle accelerators, and to particle-beam therapeutic apparatuses using the particle-beam exposure apparatuses.

2. Description of the Related Art

In a conventional particle-beam exposure apparatus using a range shifter for varying a range of a charged particle beam inside a target to be exposed, in order to reduce the variation, due to scattering in the range shifter, of the charged-particle-beam diameter, the range shifter has been placed close to the target, and a scatter device as beam scatterer as well as a set of quadrupole magnets has also been placed at the upstream side of the range shifter along the beam traveling direction (for example, referring to Patent Document 1), or a beam collimator has been placed (for example, referring to Patent Document 2).

[Patent Document 1] Japanese Laid-Open Patent Publication 212,253/2001 (Paragraph 0053, FIG. 1).

[Patent Document 2] Japanese Laid-Open Patent Publication 562/2001 (Paragraph 0025, FIG. 7).

SUMMARY OF THE INVENTION

Because the conventional particle-beam exposure apparatus is configured as above, the range shifter has had to be placed close to the target; therefore, in a case of a therapeutic apparatus using the particle-beam exposure apparatus for exposing the particle beam to the head and neck portion of a patient, because of the spatial interference with the shoulder of the patient, the range shifter cannot be drawn to the portion to be exposed, and consequently, a problem has occurred in which the charged-particle-beam diameter cannot be narrowed to a needed size. Moreover, because the range shifter whose thickness is needed to be changed during treatment has been placed dose to the patient, especially when high-speed driving of the range shifter is performed, a problem has occurred in which the patient feels intimidated by a movement noise. Furthermore, because the beam diameter at the target is almost determined by contribution of scattering in the range shifter and the target, the beam diameter cannot be narrowed by the set of quadrupole magnets or the beam collimator placed at the upstream side of the range shifter along the beam traveling direction; consequently, in the conventional apparatus, only controlling towards the direction in which the beam diameter is widened has been possible.

An objective of the present invention, which is made to solve the above described problems, is to obtain a particle-beam exposure apparatus and a particle-beam therapeutic apparatus, in which, by reducing diameter increase, due to scattering in a range shifter, of a charged particle beam, the charged particle beam whose diameter is so narrow that spatially accurate exposure into the target is possible can be supplied, as well as, by placing the range shifter at a position apart from a patient, intimidation caused by a movement noise, etc. can be prevented.

A particle-beam exposure apparatus and a particle-beam therapeutic apparatus include a range shifter for varying energy of a charged particle beam with a thickness of the range shifter being changed during exposure of the charged particle beam, so that a range of the charged, particle beam at a target to be exposed is set to a desired value; and a set of quadrupole magnets, being placed between the range shifter and the target, based on the magnetization amount of the set of quadrupole magnets being controlled corresponding to the charged-particle-beam energy varied by the range shifter, for reducing diameter increase, due to scattering at the range shifter, of the charged particle beam at the target.

According to this method, the beam diameter at the target can be set to a smaller value than that in the conventional method, and spatially accurate exposure into the target can be realized; moreover, the range shifter can be placed at a position apart from the target.

DETAILED DESCRIPTION OF THE PREFERRED EMBODIMENTS

Embodiment 1

Figure 1:
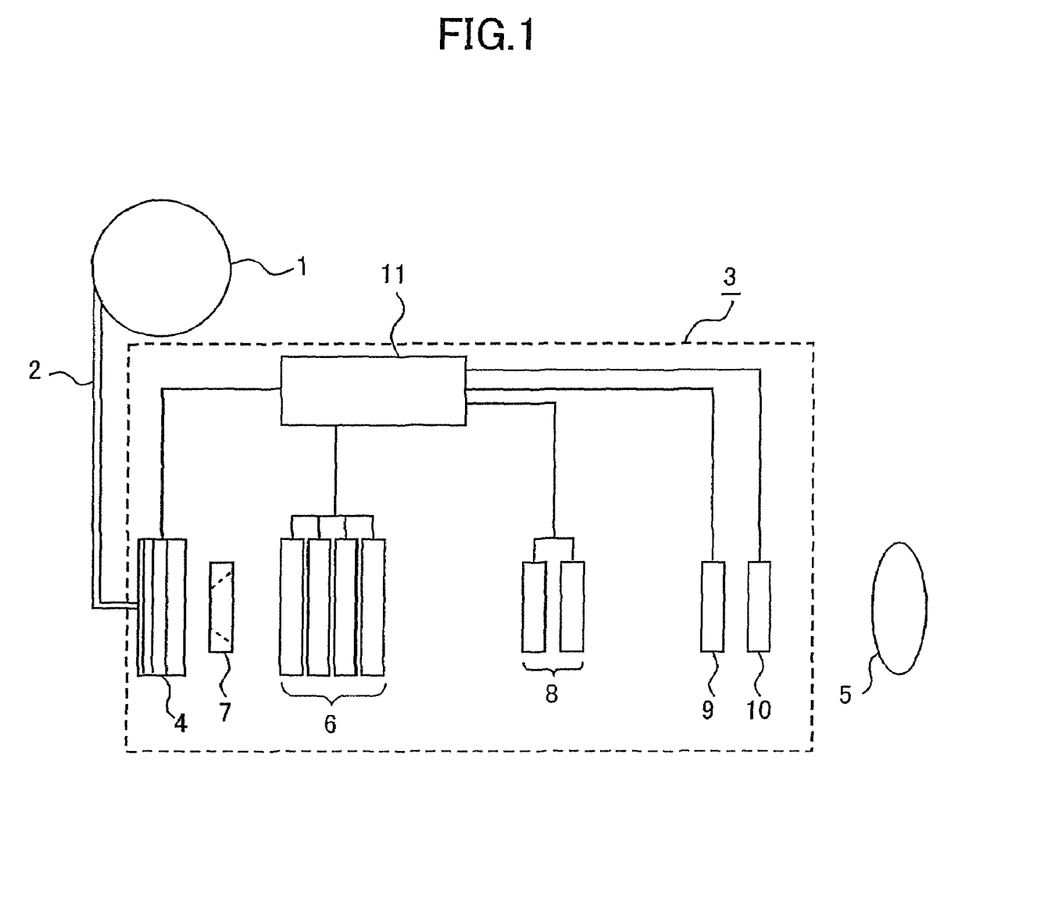
FIG. 1 is a schematic layout of units representing a particle-beam exposure apparatus and a particle-beam therapeutic apparatus according to Embodiment 1 of the present invention.

Hereinafter, a particle-beam exposure apparatus, and a particle-beam therapeutic apparatus composed of this particle-beam exposure apparatus, a particle accelerator, and a beam transport system, according to Embodiment 1 of the present invention, are explained based on FIG. 1. In FIG. 1, after a charged particle beam generated in a particle accelerator 1 is introduced into a particle-beam exposure apparatus 3 through a beam transport system 2, first, the charged particle beam passes through a variable-type range shifter 4 for decreasing, by passing through an acrylic board therein, the energy of the charged particle beam. A set of quadrupole magnets 6 for reducing diameter increase of the charged particle beam due to the variable-type range shifter 4 is placed between this variable-type range shifter 4 and a target 5 to be exposed. Moreover, a fixed-type beam slit 7, whose aperture diameter is fixed, for limiting increase of the divergence angle of the charged particle beam is placed between the variable-type range shifter 4 and the set of quadrupole magnets 6; and scanning electromagnets 8 for changing the beam orbit, a beam dose monitor 9, and a beam position monitor 10 are placed between the set of quadrupole magnets 6 and the target 5. Furthermore, the thickness of the acrylic board included in the variable-type range shifter 4, and the magnetic field strength of the scanning electromagnets 8 are controlled by an exposure controller 11.

Next, an operation of the particle-beam exposure apparatus is explained. The charged particle beam introduced to the variable-type range shifter 4 from the particle accelerator 1 through the beam transport system 2 passes through the acrylic board included in the variable-type range shifter 4; thereby, the beam energy is decreased. The variable-type range shifter 4 is configured, for example, by a plurality of acrylic boards whose thicknesses are differed from each other so that the combination of these acrylic boards can be changed, or by a wedge-shaped acrylic board so that the position where the charged particle beam passes can be changed; thereby, the thickness of the acrylic board through which the charged particle beam passes can be changed, and consequently, it can be controlled how much the particle-beam energy is decreased.

On the other hand, due to the scattering in the variable-type range shifter 4, the beam diameter of the charged particle beam is increased. The fixed-type beam slit 7 limits the divergence angle of the charged particle beam due to the scattering in the variable-type range shifter 4. Because charged particles whose divergence angles are relatively large are removed by the fixed-type beam slit 7, radio activation of the units placed at the downstream side of the fixed-type beam slit 7 along the beam traveling direction is prevented.

Moreover, exposure into the target 5 placed along an orientation perpendicular to the beam traveling direction is performed by keeping the thickness of the variable-type range shifter 4 and the magnetization amount of the set of quadrupole magnets 6 to be constant, and changing the charged-particle-beam route using the scanning electromagnets 8. When once the exposure to the orientation perpendicular to the beam traveling direction has been completed, after the thickness of the variable-type range shifter 4 and the magnetization of the set of quadrupole magnets are changed by the exposure controller 11, exposure using the scanning electromagnets 8 is performed again. By repeating this operation, exposure is performed into the target 5 along the beam traveling direction and along the orientation perpendicular to this direction.

The beam dose monitor 9 is used for determining the timing of changing the charged-particle-beam exposing position on the target 5; meanwhile, the beam position monitor 10 is used for moving the charged particle beam to the correct position, which is used together with the scanning electromagnets 8. These operations are similar to those in the conventional technology.

Next, the reducing of the increase of the charged-particle-beam diameter by using the set of quadrupole magnets is explained. As described above, when the charged particle beam passes through the variable-type range shifter 4, the beam diameter of the charged particle beam increases. When the charged particle beam passes through the target 5, the beam diameter also increases similarly; therefore, given that the beam diameter is $\sigma_0$ when the variable-type range shifter 4 and the target 5 are not placed, the increase of the beam diameter due to the variable-type range shifter 4 is $\sigma_{RS}$, and the increase of the beam diameter due to the target is $\sigma_t$, the beam diameter $\sigma$ at the target 5 is given by the following equation.

$$\sigma^2 = \sigma_0^2 + \sigma_{RS}^2 + \sigma_t^2 \quad \text{[Eq. 1.]}$$

Therefore, when the thickness of the acrylic board included in the variable-type range shifter 4 or the range of the charged particle beam at the target 5 increases, relative contribution of $\sigma_0$, which is adjustable using a unit placed at the upstream side of the variable-type range shifter 4 along the beam traveling direction, to $\sigma$ decreases; therefore, the beam diameter at the target 5 cannot be decreased using the unit placed at the upstream side of the variable-type range shifter 4.

Because when a device for focusing the charged particle beam is not provided between the variable-type range shifter 4 and the target 5, the beam diameter at the target 5 increases in proportional to the product of the distance from the variable-type range shifter 4 to the target 5 and the divergence angle due to the scattering in the variable-type range shifter 4, in order to reduce the increase of $\sigma$, it is unavoidable to draw the variable-type range shifter 4 dose to the target 5; therefore, when the apparatus is applied to a therapeutic apparatus, a problem occurs, for example, in which a patient feels intimidated by a movement noise from the variable-type range shifter 4.

Therefore, by using the set of quadrupole magnets 6 placed between the variable-type range shifter 4 and the target 5, $\sigma_{RS}$ is decreased by focusing the divergence of the charged particle beam due to the scattering in the variable-type range shifter 4. Although, in this example, a quartet set of quadrupole magnets is used as the set of quadrupole magnets, a triplet set of quadrupole magnets, for example, may be used. Here, using the exposure controller 11, the magnetization amount of the set of quadrupole magnets 6 is set to a value determined by the charged-particle-beam energy supplied from the particle accelerator and the thickness of the variable-type range shifter 4.

By using this method, the beam diameter at the target 5 can be set to a smaller value than that in the conventional method, and spatially accurate exposure to the target can be realized. Moreover, because the variable-type range shifter 4 can be placed at a position apart from the target 5, the problem of the intimidation to the patient by the therapeutic apparatus does not occur; therefore, by high-speed driving of the variable-type range shifter 4, the charged-particle-beam energy can be varied high-speedily.

Because scattering effect of the variable-type range shifter 4 can be surely prevented, by setting the maximum thickness of the variable-type range shifter 4 thicker than that in the conventional method, the energy variable range of the charged particle beam using the range shifter can be more extended, than that in the conventional method; thereby, the number of operations for changing the energy outputted from the particle accelerator that supplies the charged particle beam can be reduced.

Figure 2:
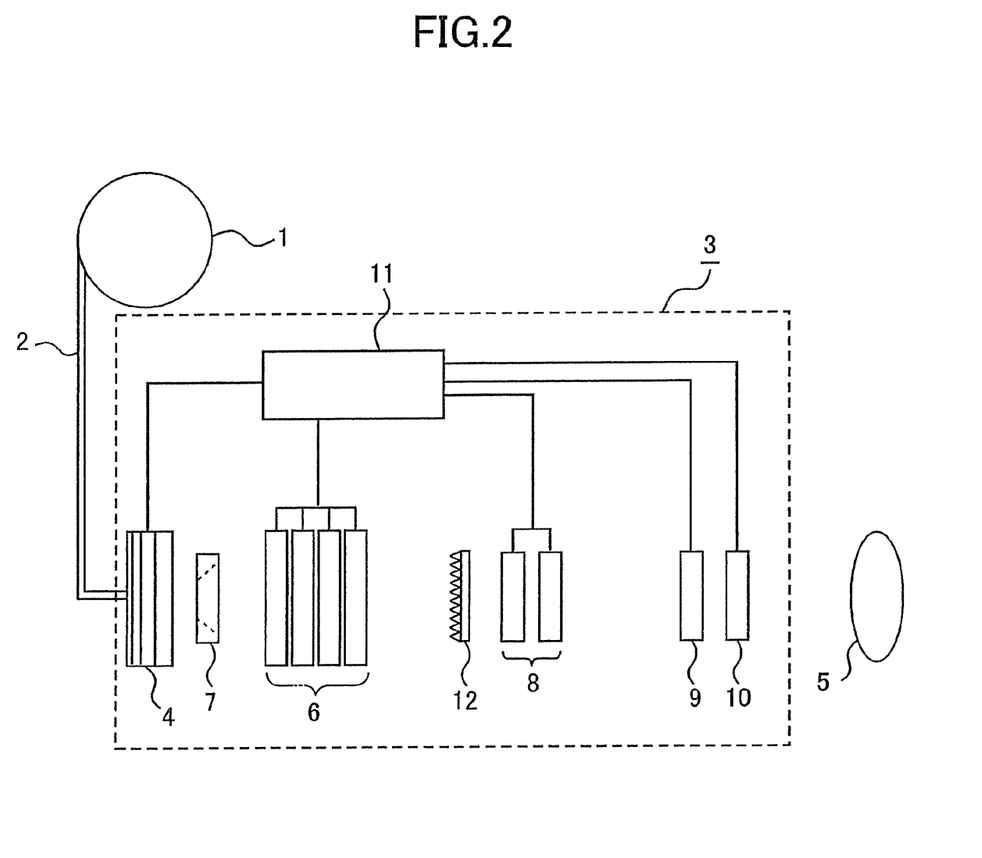
FIG. 2 is another schematic layout of units representing the particle-beam exposure apparatus and the particle-beam therapeutic apparatus according to Embodiment 1 of the present invention.

Moreover, as represented in FIG. 2, a ridge filter 12 may be additionally provided for broadening the Bragg peak, so that the forming of the spread-out Bragg peak (SOBP) may be enabled to be effectively performed using the variable-type range shifter 4. According to the present invention, by using the set of quadrupole magnets 6 placed between the variable-type range shifter 4 and the target 5, and by focusing the divergence of the charged particle beam due to the scattering in the variable-type range shifter 4, as represented in FIG. 2, the ridge filter 12 can be placed at the upstream side of the scanning electromagnets 8 along the beam traveling direction. By placing the ridge filter 12 at the upstream side of the scanning electromagnets 8 along the beam traveling direction, it can be configured in such a way that the charged particle beam passes through a predetermined area of the ridge filter; therefore, deterioration of the Bragg-peak uniformity based on the ridge structure can be prevented.

Furthermore, by using the set of quadrupole magnets 6 placed between the variable-type range shifter 4 and the target 5, and by focusing the divergence of the charged particle beam due to the scattering in the variable-type range shifter 4, the increase of the charged-particle-beam diameter in the variable-type range shifter 4 can be reduced; thereby, an allowable value in response to the increase of the charged-particle-beam diameter due to the scattering in the ridge filter 12 becomes larger than that in the conventional apparatus, and the range where the ridge height of the ridge filter 12 is selected extends.

Embodiment 2

Figure 3:
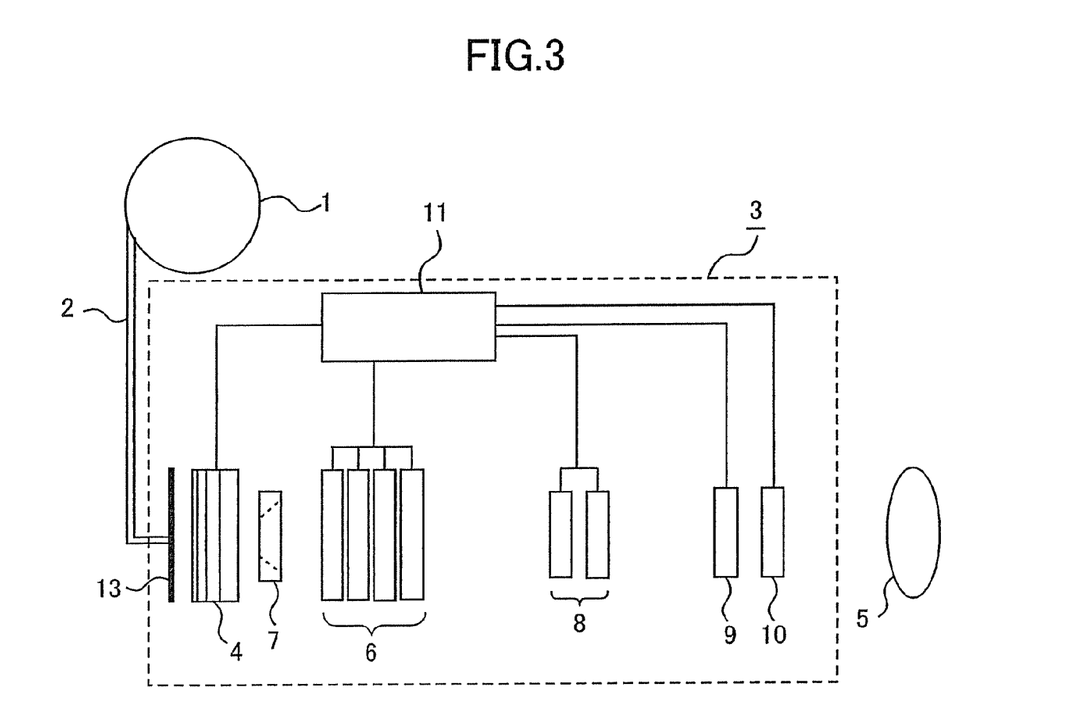
FIG. 3 is a schematic layout of units representing a particle-beam exposure apparatus and a particle-beam therapeutic apparatus according to Embodiment 2 of the present invention.

If the acrylic board is not inserted into the variable-type range shifter 4, the divergence at the variable-type range shifter 4 is prevented; however, thus, when the varying of the divergence angle at the variable-type range shifter 4 is widened, the beam-diameter control becomes complicated. In a particle-beam exposure apparatus and a particle-beam therapeutic apparatus according to Embodiment 2, as represented in FIG. 3, by providing a thin beam scatterer 13 composed of, for example, a tungsten or a lead thin film, even when the acrylic board is not inserted into the variable-type range shifter 4, the divergence angle of the charged particle beam being incident onto the set of quadrupole magnets 6 is made to be widened; thereby, the varying ratio of the divergence angle due to varying of the thickness of the acrylic board included in the variable-type range filter 4 is made to be relatively small. By providing the beam scatterer 13, it is prevented that the magnetization amount of the set of quadrupole magnets significantly varies depending on the thickness of the variable-type range shifter 4; thus, the exposing control can be easily performed.

Embodiment 3

Figure 4:
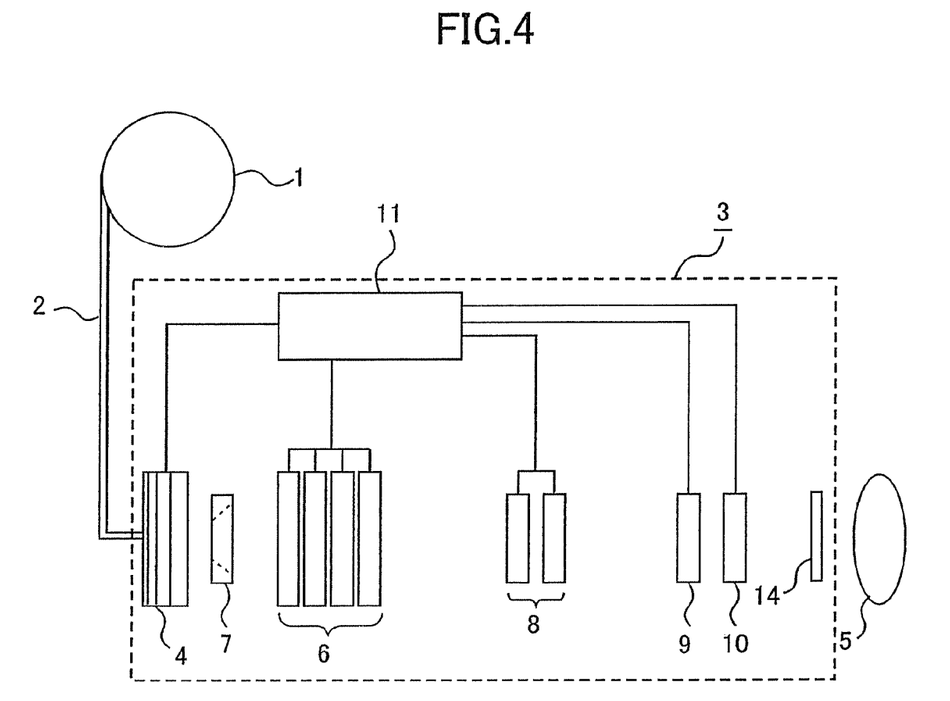
FIG. 4 is a schematic layout of units representing a particle-beam exposure apparatus and a particle-beam therapeutic apparatus according to Embodiment 3 of the present invention.

In Embodiment 1, in order to decrease the charged-particle-beam energy, the case in which only the variable-type range shifter 4 provided at the upstream side apart from the target 5 along the beam traveling direction is used has been explained; however, as represented in FIG. 4, by providing a fixed-type range shifter 14 close to the target 5, the charged-particle-beam energy being incident onto the target 5 can also be decreased at the downstream side of the set of quadrupole magnets 6 along the beam traveling direction. When the charged-particle-beam energy is decreased using the variable-type range shifter 4 into a value where the beam is stopped at the surface proximity of the target 5, because the momentum width of the charged particle beam passing through the variable-type range shifter 4 significantly increases, the beam focusability of the set of quadrupole magnets 6 decreases due to the effect of the chromatic aberration; accordingly, the charged-particle-beam diameter at the target 5 cannot be narrowed.

Therefore, varying width of the charged-particle-beam energy is regulated by the variable-type range shifter 4 placed at the upstream side of the set of quadrupole magnets 6 along the beam traveling direction, where the regulating width is set at a range in which affection that the beam focusability by the set of quadrupole magnets 6 is decreased due to the chromatic aberration does not occur, and, on the other hand, the charged-particle-beam energy is also decreased to a predetermined value by the fixed-type range shifter 14 placed at the downstream side of the set of quadrupole magnets 6 along the beam traveling direction. Here, because the varying width of the decrease of the charged-particle-beam energy is regulated by the variable-type range shifter 4 during an exposure unit, regarding the fixed-type range shifter 14, the thickness is needless to be changed during the exposure. Regarding different exposure units, when the decreasing widths of the charged-particle-beam energy are significantly differed from each other, the thickness of the fixed-type range shifter 14 becomes necessary to be changed.

According to the configuration in which, in addition to the variable-type range shifter 4 placed at the upstream side of the set of quadrupole magnets 6 along the beam traveling direction, the fixed-type range shifter 14 is placed close to the target 5 that is placed, at the downstream side of the set of quadrupole magnets 6 along the beam traveling direction, the momentum width of the charged particle beam being incident onto the set of quadrupole magnets 6 is limited, and the problem of the chromatic aberration is prevented; thereby, the charged particle beam having relatively narrow beam diameter can be exposed from the inside to the surface proximity of the target 5.

Embodiment 4

Figure 5:
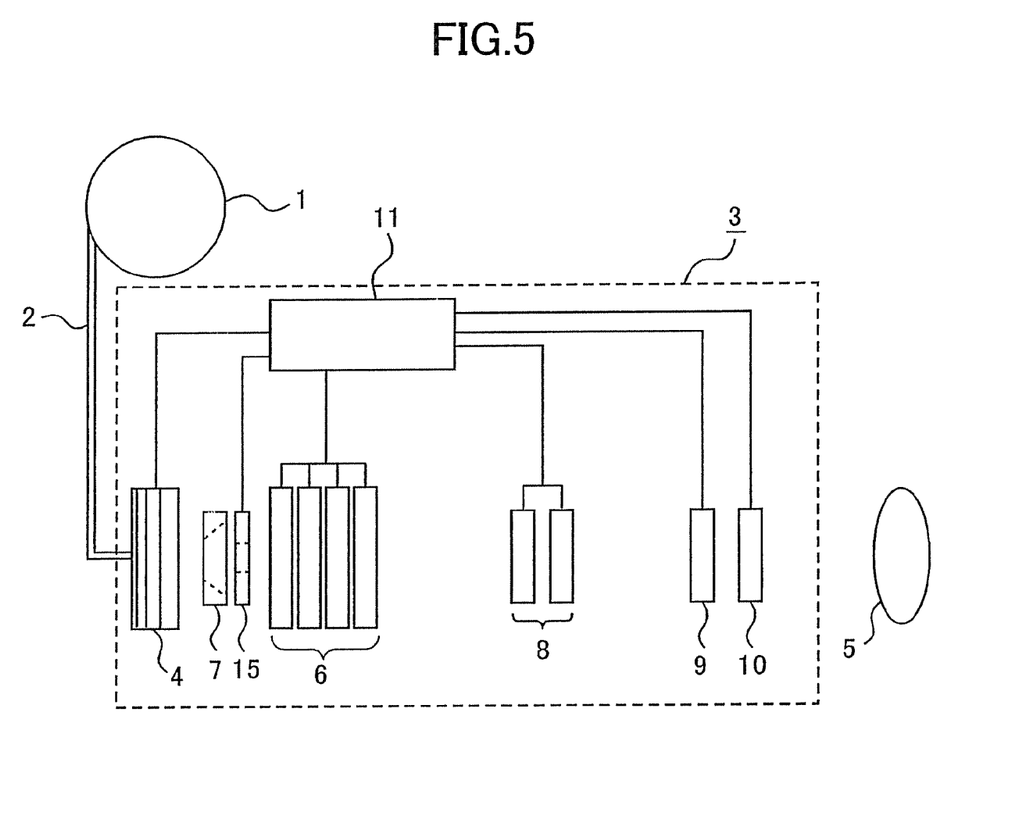
FIG. 5 is a schematic layout of emits representing a particle-beam exposure apparatus and a particle-beam therapeutic apparatus according to Embodiment 4 of the present invention.

By providing a beam slit for reducing the charged-particle-beam emittance instead, of providing the fixed-type range shifter 14 at the downstream side of the set of quadrupole magnets 6 along the beam traveling direction as described in, Embodiment 3, the problem can also be solved in which the charged-particle-beam diameter increases due to the chromatic aberration at the set of quadrupole magnets 6. FIG. 5 is a view illustrating a configuration of a particle-beam exposure apparatus and a particle-beam therapeutic apparatus according to this Embodiment 4, in which, in response to the configuration represented in FIG. 1, a variable-type beam slit 15 whose aperture diameter is variable is additionally provided at the upstream side of the set of quadrupole magnets 6 along the beam traveling direction, so that the increase of the charged-particle-beam divergence angle due to the scattering in the variable-type range shifter 4 is controlled. The aperture diameter of the variable-type beam slit 15 is controlled by the exposure controller 11 depending on the thickness of the variable-type range shifter 4.

When the charged-particle-beam energy is decreased using the variable-type range shifter 4 into a value where the beam is stopped at the surface proximity of the target 5, the charged-particle-beam emittance is reduced by the variable-type beam slit 15, so that the increase of the charged-particle-beam diameter due to the chromatic aberration at the set of quadrupole magnets 6 is cancelled out. Because the fixed-type range shifter 14 described in Embodiment 3 becomes unnecessary by using the variable-type beam slit 15, intimidation that a patient feels can be further reduced in the therapeutic apparatus.

Here, the number of the charged particles reaching the target 5 decreases by the variable-type beam slit 15; however, because, only when the charged particle beam exposes the surface proximity of the target 5 where the number of the exposing particles required is relatively small, a part of the charged particle beam is removed by the variable-type beam slit 15, it is not a problem that the number of the charged particles decreases.

What is claimed:
1. A particle-beam exposure apparatus comprising:
a variable-type range shifter for decreasing energy of a charged particle beam;
a quadrupole magnet positioned downstream of the variable-type range shifter and controlled such that a magnetization amount of the quadrupole magnet corresponds to the charged-particle-beam energy decreased by the variable-type range shifter, for reducing the divergence of the charged particle beam due to scattering at the variable-type range shifter; and scanning electromagnets for changing a beam orbit of the charged particle beam.

2. A particle-beam exposure apparatus as recited in claim 1 wherein the scanning electromagnets change the beam orbit keeping the magnetization amount of the quadrupole magnet constant.

3. A particle-beam exposure apparatus as recited in claim 1 further comprising:
   a fixed-type beam slit having a fixed aperture diameter, wherein said fixed-type beam slit is placed between the variable-type range shifter and the quadrupole magnet, for limiting increase of a divergence angle of the charged particle beam.

4. A particle-beam exposure apparatus as recited in claim 1 wherein the variable-type range shifter comprises a plurality of acrylic boards, each acrylic board having a different thickness.

5. A particle-beam therapeutic apparatus comprising:
   a particle accelerator for generating a charged particle beam;
   a particle-beam exposure apparatus, the particle-beam exposure apparatus including:
   a variable-type range shifter for decreasing energy of a charged particle beam,
   a quadrupole magnet positioned downstream of the variable-type range shifter, and controlled such that a magnetization amount of the quadrupole magnet corresponds to the charged-particle-beam energy decreased by the variable-type range shifter, for reducing the divergence of the charged particle beam due to scattering at the variable-type range shifter,
   scanning electromagnets for changing a beam orbit of the charged particle beam; and
   a beam transport system for transporting the charged particle beam into the particle-beam apparatus.

6. A particle-beam therapeutic apparatus as recited in claim 5, wherein the scanning electromagnets change the beam orbit keeping the magnetization amount of the quadrupole magnet constant.

7. A particle-beam therapeutic apparatus as recited in claim 5, further comprising:
   a fixed-type beam slit having a fixed aperture diameter, wherein said fixed-type beam slit is placed between the variable-type range shifter and the quadrupole magnet, for limiting increase of a divergence angle of the charged particle beam.

8. A particle-beam therapeutic apparatus as recited in claim 5 wherein the variable-type range shifter comprises a plurality of acrylic boards, each acrylic board having a different thickness.

* * * * *